United States Patent [19]

Köppe et al.

[11] 4,016,202
[45] Apr. 5, 1977

[54] 1-PHENOXY-2-HYDROXY-3-ALKYNYLAMINO-PROPANES AND SALTS THEREOF

[75] Inventors: Herbert Köppe; Werner Kummer; Helmut Stähle; Gojko Muacevic, all of Ingelheim am Rhein, Germany

[73] Assignee: Boehringer Ingelheim GmbH, Ingelheim am Rhein, Germany

[22] Filed: Sept. 3, 1975

[21] Appl. No.: 609,998

Related U.S. Application Data

[63] Continuation-in-part of Ser. No. 444,713, Feb. 22, 1974, Pat. No. 3,925,446.

[30] Foreign Application Priority Data

Feb. 28, 1973 Germany ............ 2309887
Jan. 26, 1974 Germany ............ 2403809

[52] U.S. Cl. ............ 260/501.17; 260/253; 260/501.19; 260/570 R; 260/570.7
[51] Int. Cl.² ............ C07C 93/06
[58] Field of Search ............ 260/570.7, 570 R, 253, 260/501.17, 501.19

[56] References Cited

UNITED STATES PATENTS

| | | | |
|---|---|---|---|
| 3,459,782 | 8/1969 | Koppe et al. | 260/465 |
| 3,541,130 | 11/1970 | Koppe et al. | 260/465 |
| 3,712,927 | 1/1973 | Howe et al. | 260/465 X |

*Primary Examiner*—Dolph H. Torrence
*Attorney, Agent, or Firm*—Hammond & Littell

[57] ABSTRACT

Racemic and optically active compounds of the formula

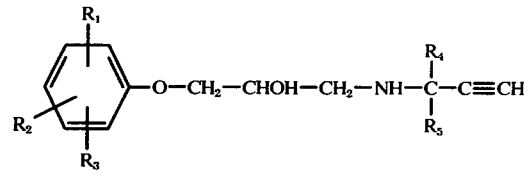

wherein $R_1$ is hydrogen; halogen; nitro; alkyl of 1 to 5 carbon atoms; alkoxy of 1 to 4 carbon atoms; alkenyl of 2 to 5 carbon atoms; alkynyl of 2 to 5 carbon atoms; alkylamino of 1 to 5 carbon atoms; dialkylamino of 1 to 5 carbon atoms in each alkyl; alkoxyalkyl of 2 to 6 carbon atoms; alkylamino-alkyl of 2 to 6 carbon atoms; dialkylaminoalkyl of 3 to 12 carbon atoms; $-(CH_2)_x-NH_2$, $-(CH_2)_x-OH$, all where $x$ is an integer from 0 to 3; $-COOH$; $-COOR_6$, where $R_6$ is alkyl of 1 to 4 carbon atoms; alkynyloxy of 3 to 6 carbon atoms; alkenyloxy of 3 to 6 carbon atoms; $-CO-R_9$, $-O-CO-R_9$, $-NH-CO-R_9$, all where $R_9$ is alkyl of 1 to 6 carbon atoms, phenylalkyl of 7 to 10 carbon atoms or phenyl; cycloalkyl of 3 to 7 carbon atoms; $-Q-CO-NR_7R_8$, where Q is a single bond, oxygen, $-NH-$, $-CH_2-$ or $-CH_2-NH-$, and $R_7$ and $R_8$ are hydrogen, lower alkyl or, taken together with the nitrogen, pyrrolidino, piperidino or morpholino; phenyl; phenyl substituted with a substituent selected from the group consisting of halogen, lower alkyl, lower alkoxy, nitro, cyano and carboxyl; phenoxy; or phenoxy substituted with a substituent selected from the group consisting of halogen, lower alkyl, lower alkoxy, nitro, cyano and carboxyl;

$R_2$ is hydrogen, halogen, alkyl of 1 to 4 carbon atoms, alkoxy of 1 to 4 carbon atoms, alkanoyl of 2 to 4 carbon atoms, alkenyl of 2 to 4 carbon atoms, amino, nitro or, together with $R_1$, 3,4-methylenedioxy;

$R_3$ is hydrogen, halogen, alkyl of 1 to 4 carbon atoms, alkoxy of 1 to 4 carbon atoms or, together with $R_2$ in the ortho-position, $-CH=CH-CH=CH-$ or $-(CH_2)_n-$, where $n$ is an integer from 3 to 5;

$R_4$ is hyddrogen or alkyl of 1 to 3 carbon atoms; and $R_5$ is alkyl of 1 to 3 carbon atoms or, together with $R_4$, $-(CH_2)_p-$ where $p$ is an integer from 4 to 6; and physiologically compatible acid addition salts thereof. The compounds as well as their salts are useful as adrenolytics and hypotensives.

15 Claims, No Drawings

1-PHENOXY-2-HYDROXY-3-ALKYNYLAMINO-PROPANES AND SALTS THEREOF

This is a continuation-in-part of copending application Ser. No. 444,713 filed Feb. 22, 1974, now U.S. Pat. No. 3,925,446 granted Dec. 9, 1975

This invention relates to novel 1-phenoxy-2-hydroxy-3-alkynylamino-propanes and acid addition salts thereof, as well as to various methods of preparing these compounds.

More particularly, the present invention relates to a novel class of racemic and optically active 1-phenoxy-2-hydroxy-3-alkynylamino-propanes represented by the formula

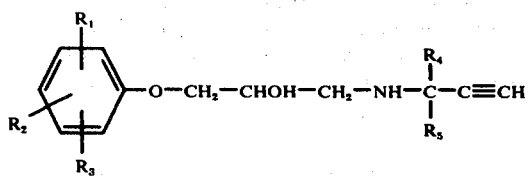

wherein $R_1$ is hydrogen; halogen; nitro; alkyl of 1 to 5 carbon atoms; alkoxy of 1 to 4 carbon atoms; alkenyl of 2 to 5 carbon atoms; alkynyl of 2 to 5 carbon atoms; alkylamino of 1 to 5 carbon atoms; dialkylamino of 1 to 5 carbon atoms in each alkyl; alkoxyalkyl of 2 to 6 carbon atoms; alkylamino-alkyl of 2 to 6 carbon atoms; dialkylaminoalkyl of 3 to 12 carbon atoms; —$(CH_2)_x$—$NH_2$, —$(CH_2)_x$—OH, all where $x$ is an integer from 0 to 3; —COOH; —$COOR_6$, where $R_6$ is alkyl of 1 to 4 carbon atoms; alkynyloxy of 3 to 6 carbon atoms; alkenyloxy of 3 to 6 carbon atoms; —CO—$R_9$, —O—CO—$R_9$, —NH—CO—$R_9$, all where $R_9$ is alkyl of 1 to 6 carbon atoms, phenylalkyl of 7 to 10 carbon atoms or phenyl; cycloalkyl of 3 to 7 carbon atoms; —Q—CO—$NR_7R_8$, where Q is a single bond, oxygen, —NH—, —$CH_2$— or —$CH_2$—NH—, and $R_7$ and $R_8$ are hydrogen, lower alkyl or, taken together with the nitrogen, pyrrolidino, piperidino or morpholino; phenyl; phenyl substituted with a substituent selected from the group consisting of halogen, lower alkyl, lower alkoxy, nitro, cyano and carboxyl; phenoxy; or phenoxy substituted with a substituent selected from the group consisting of halogen, lower alkyl, lower alkoxy, nitro, cyano and carboxyl;

$R_2$ is hydrogen, halogen, alkyl of 1 to 4 carbon atoms, alkoxy of 1 to 4 carbon atoms, alkanoyl of 2 to 4 carbon atoms, alkenyl of 2 to 4 carbon atoms, amino, nitro or, together with $R_1$, 3,4-methylenedioxy;

$R_3$ is hydrogen, halogen, alkyl of 1 to 4 carbon atoms, alkoxy of 1 to 4 carbon atoms or, together with $R_2$ in the ortho-position, —CH=CH—CH=CH— or —$(CH_2)_n$—, where $n$ is an integer from 3 to 5;

$R_4$ is hydrogen or alkyl of 1 to 3 carbon atoms; and $R_5$ is alkyl of 1 to 3 carbon atoms or, together with $R_4$, —$(CH_2)_p$— where $p$ is an integer from 4 to 6; and physiologically compatible acid addition salts thereof.

If $R_1$ represents a lower aliphatic acyl group, lower alkanoyl, such as the acetyl, propionyl, butyryl or isobutyryl group, may, for example, be considered here. As araliphatic acyl group, $R_1$ may represent phenylalkanoyl, such as the phenacetyl group, which is optionally substituted at the phenyl with one or several halogen atoms, alkyl groups, nitro, cyano or carboxyl groups. If $R_1$ represents aromatic acyl, it may be, for example, a benzoyl group optionally substituted once or several times by halogen, lower alkyl, nitro, cyano or carboxyl.

If $R_1$ represents an acyloxy or acylamino group, the acyl group therein may as well be represented by the acyl groups individually listed in the above paragraph.

The novel compounds may be produced in a number of ways, in which the following are representative:

a. Reacting a compound of general formula II

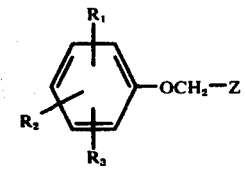

where $R_1$ to $R_3$ are defined as in formula I and Z is

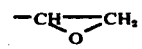

or —CHOH—$CH_2$—Hal (Hal = halogen), with an amine of general formula

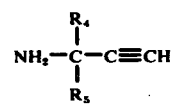

where $R_4$ and $R_5$ have the meanings indicated in formula I;

b. Cleaving an easily removable protective group off compounds of general formula IV

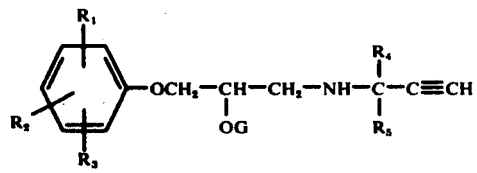

where $R_1$ to $R_5$ are defined as in formula I and G is an easily hydrogenolytically removable group, for example, an acyl or an acetal group.

c. Cleaving a protective group off a compound of general formula V

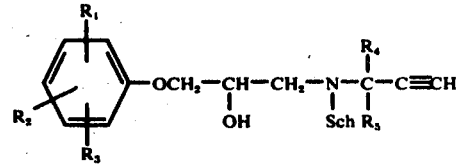

where $R_1$ to $R_5$ are defined as in formula I and Sch is an easily removable protective group, for example, an acyl group or the carbobenzoxy group;

d. Hydrolyzing an oxazolidine derivative of general formula VI

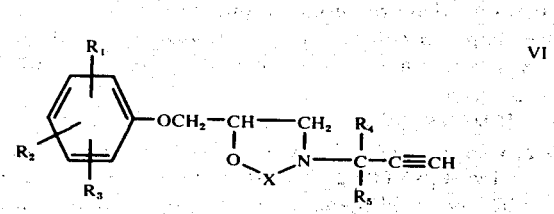

where $R_1$ to $R_5$ are defined as in formula 1, and X represents —CO—, —CH$_2$— or a —CH—lower alkyl group, for example, with sodium hydroxide or potassium hydroxide solution in water or in an alcohol/water mixture.

In addition, other processes for the production of compounds of formula I are possible, such as converting a compound having already the 3-alkynylaminopropanol-2 side chain, but not having one of the substituents $R_1$, $R_2$ or $R_3$ on the phenyl ring and in place thereof another substituent convertible to the desired substituent, to the desired substituent $R_1$, $R_2$ or $R_3$ by conventional methods.

e. Converting compounds of formula VIIa

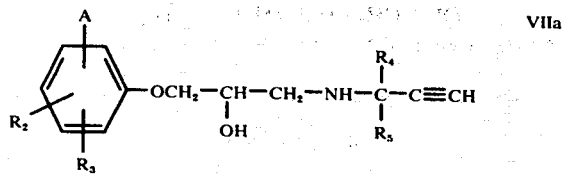

where $R_2$ to $R_5$ are defined as in formula I and A is a group convertible in line with conventional methods, such as the —CONH$_2$ or —COOR$_6$ group (whereby $R_6$ is defined as in formula I), an alkoxy, O-acyl or NO$_2$ group, or compounds of general formula VIIb

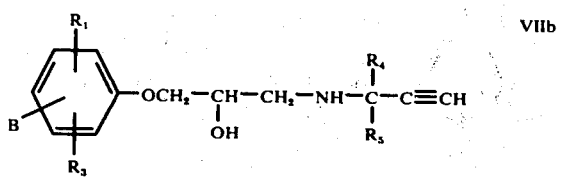

where $R_1$ and $R_3$ to $R_5$ are defined as in formula I and B is a group convertible into $R_2$ in line with conventional methods, into compounds of formula I, using the method required in each case (splitting off water, reducing, saponifying, cleaving an ether, alkylating).

Furthermore, the following process is suitable for producing compounds of general formula I, where $R_2$ or $R_3$ is a halogen atom:

f. Introducing a halogen atom into compounds of formula VIII

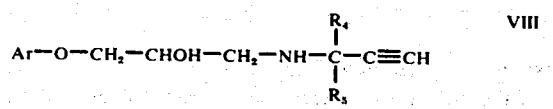

where $R_4$ and $R_5$ are defined as in formula I, and Ar is a group of the partial formula

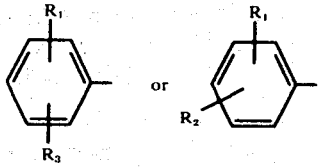

(where $R_1$, $R_2$ and $R_3$ have the above meanings), for example, with a mixture of hydrogen halide and hydrogen peroxide at elevated temperature.

The starting compounds required for carrying out the processes (a) to (f) have already been partly known. The remainder can be obtained by known processes. Thus, the epoxides of formula II may be produced easily by reaction with a corresponding phenol or phenolate of formula X

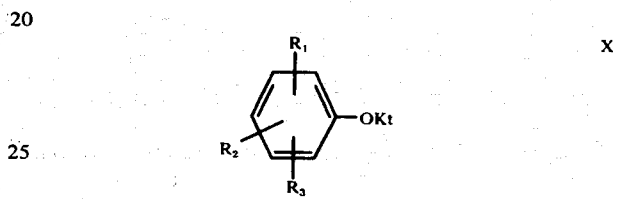

where $R_1$ to $R_3$ have the meanings mentioned above and Kt is hydrogen or a cation (e.g., an alkali metal cation). The epoxides may be used for production of further starting materials; for instance, the halogen hydrins of formula II may be produced by reacting the epoxides with the corresponding hydrogen halide.

Amines of formula III have been known and represent mostly commerical products. Compounds of formula IV may be obtained by reacting a halohydrin of formula II with a compound (such as vinyl ether or dihydropyran) to give the protective group G and, subsequently, reacting the obtained compound of formula

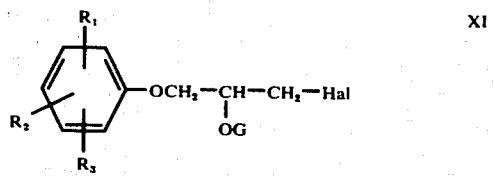

with a compound of general formula III.

The tertiary amines of formula V are obtained by reacting a compound of general formula X with a compound of general formula

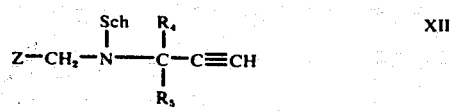

where $R_4$, $R_5$ and Sch have the above-mentioned meanings and Z is a halide.

The oxazolidinones of formula VI (e.g., compounds where X = CO) are producible, for example, starting from the epoxides of formula II, by reacting the latter with a urethane (producible from a chloroethyl formate and an amine of formula II) of formula

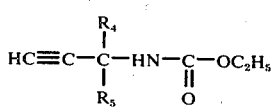

XIII where $R_4$ and $R_5$ have the meanings mentioned above.

The compounds of formulas VIIa, VIIb and VIII already contain the complete 1-phenoxy-2-hydroxy-3-alkynylamino-propane structure and may, therefore, be produced analogously to the process (a) described above, starting from the corresponding phenol, via the corresponding 1-phenoxy-2,3-epoxypropane (producible by reaction with epichlorohydrin) by reaction with an alkynylamine of formula III.

The compounds according to the invention possess an asymmetric carbon atom at the CHOH group and can occur, therefore, as racemates as well as in the form of optical antipodes. The latter may be obtained by separation of racemates with the conventional optically active acids, such as dibenzoyl- (or di-p-toluyl-)D-tartaric acid or D-3-bromocamphor-8 sulfonic acid or by using optically active starting materials as well.

The 1-aryloxy-2-hydroxy-3-alkynylamino-propanes of general formula I according to the invention may be converted into the physiologically compatible acid addition salts thereof in the conventional way. Suitable acids are, for example, hydrochloric acid, hydrobromic acid, sulfuric acid, methane-sulfonic acid, maleic acid, acetic acid, oxalic acid, lactic acid, tartaric acid or 8-chlorotheophylline.

The compounds of general formula I or the physiologically compatible acid addition salts thereof have shown valuable therapeutic properties, in particular, adrenolytic properties as demonstrated by animal tests in guinea pigs and may, therefore, be used for treatment or prophylaxis of diseases of the coronaries and for treatment of cardiac arrhythmia, especially of tachycardia, in human medicine. The blood-pressure decreasing properties of the compounds are therapeutically interesting too. Compared to the known $\beta$-receptor blockers, for example, the commercial product 1-(1-naphthyloxy)-2-hydroxy-3-isopropylaminopropane (Propranolol), the compounds have the advantage of a considerably decreased toxicity combined with a superior action.

The invention, therefore, also relates to a process for the treatment of coronary diseases, cardiac arrhythmia and high blood pressure in warm-blooded animals comprising administering a safe but effective amount of the 1-aryloxy-2-hydroxy-3-alkynylamino-propane compounds of formula I.

Here compounds of general formula I have proved to be valuable, in particular, where $R_4$ and $R_5$ represent each a methyl group and one of $R_1$, $R_2$ and $R_3$ is other than hydrogen (substituted 1-phenoxy-3-(2-methylbutynyl-3-amino-2)-2-propanols).

Among the preferred meanings for $R_1$ are to be stressed the unsaturated substituents such as alkenyl (e.g., allyl), alkynyl (e.g., ethynyl, propynyl), alkenyloxy (e.g., allyloxy) or alkynyloxy (e.g., propargyloxy) in particular, if they stand in the 2-position to the propanolamine side-chain.

$R_2$ may represent in this case preferably hydrogen, but furthermore, lower alkyl (e.g., methyl), preferably in the 5-position to the propanolamine side-chain, while $R_3$ is hydrogen as a rule. $R_4$ and $R_5$ are again preferably methyl.

A further preferred sub-group is formed by such substances of general formula I, where $R_1$ represents a hydroxyalkyl, in particular, the hydroxymethyl group; or an amino or acylamino, especially acetylamino group; whereby $R_2$ $R_3$ may represent in the first case hydrogen, in the second case hydrogen or else halogen or lower alkyl. $R_4$ and $R_5$ are again preferably methyl.

Important individual compounds are, in particular: 1-(2-ethynylphenoxy)-3-(2-methylbutynyl-3-amino-2)-2-propanol, 1-(2-allylphenoxy)-3-(2-methylbutynyl-3-amino-2)-2-propanol, furthermore, 1-(3,5-dibromo-4-aminophenoxy)-3-(2-methylbutynyl -3- amino-2)-2-propanol, 1-(2-hydroxymethyl-phenoxy)-2-(2-methylbutynyl-3-amino-2)-2-propanol, the 1-(3-chlorophenoxy)-3-(2-methylbutynyl-3-amino-2)-2-propanol and the 1-(4-acetamidophenoxy)-3-(2-methylbutynyl-3-amino-2)-2-propanol or the physiologically compatible acid addition salts thereof.

The single dose of the compounds according to the invention lies at 1 to 300 mg, preferably 5 to 100 mg (orally) or 1 to 20 (parenterally). When administered to warm-blooded animals, the single dosage is from 0.015 mg to 5 mg/kg.

The active ingredients according to the invention may be incorporated into the conventional galenic forms of administration, such as tablets, coated tablets, solutions, emulsions, powders, capsules or forms of sustained release. For the production of the above, the usual pharmaceutical excipients as well as the conventional methods of production may be applied.

Corresponding tablets may be obtained by mixing the active ingredients with known excipients, for example, with inert diluents, such as calcium carbonate, calcium phosphate or lactose, disintegrants, such as corn starch or alginic acid, binders, such as starch or gelatin, lubricants, such as magnesium stearate or talc and/or agents for obtaining sustained release, such as carboxypolymethylene, carboxymethylcellulose, cellulose acetate/phthalate or polyvinylacetate.

The tablets may also be composed of several layers. There may be produced correspondingly coated tablets by means of coating cores, prepared analogous to the tablets, with agents usually applied for tablet-coats, such as polyvinylpyrrolidone or shellac, gum arabic, talc, titanium dioxide or sugar. For obtaining sustained release or in order to avoid incompatibilities, the core may consist of several layers as well. Thus, the tablet coat for obtaining sustained release may also consist of several layers, whereby the excipients mentioned above for tablets may be used.

Drinks of the active ingredients or active ingredient combinations according to the invention may additionally contain a sweetener, such as saccharin, cyclamate, glycerin or sugar, as well as an agent improving the taste, for example, a flavor, such as vanilla or orange extract. Besides they may comprise suspension auxiliaries or thickeners, such as sodium carboxymethylcellulose, wetting agents, such as condensation products of fatty alcohols with ethylene oxide, or protective substances, such a p-hydroxybenzoates.

Injectable solutions are produced in the conventional way, such as under addition of preservation agents, such as p-hydroxybenzoates, or stabilizers, such as "Komplexonen" (the sodium salt of ethylene diaminetetraacetic acid), and filled into injection vials or ampoules.

Capsules containing the active ingredients or active ingredient combinations may be produced, for example, by admixing the active ingredients with inert carriers, such as lactose or sorbitol, and filling same into gelatin capsules.

Suitable suppositories may be produced by mixing the active ingredients or active ingredient combinations envisaged for same with conventional carriers, such as neutral fats or polyoxyethyleneglycol or its derivatives.

The compounds of the invention are suitable as well for combination with other pharmacodynamically active substances, such as, for example, coronary dilatators, sympathicomimetics, cardiac glycosides or tranquilizers.

The following examples illustrate the invention without restricting same in any manner.

EXAMPLE 1

1-α-Naphthoxy-3-(3-ethylpentynyl-4-amino-3)-2-propanol . HCl (according to process [a]) (I, $R_1$ = H, $R_2 + R_3$ = —CH=CH—CH=CH—, $R_4$ and $R_5$ = $C_2H_5$)

10 Grams (0.05 mol) of 1-α-naphthoxy-2,3-epoxypropane were dissolved in 80 ml of ethanol. 5.55 Grams (0.05 mol) of 3-ethyl-3-amine-pentyne-4 were added and the mixture was refluxed for two hours at boiling temperature. After having cooled off, the solvent was distilled off. The residue was dissolved in ether and acidified with alcoholic HCl. The crystallizable compound was isolated and recrystallized from a mixture of acetonitrile and ethanol Yield: 9.5 gm, m.p. 195° to 196° C.

EXAMPLE 2

1-m-Tolyloxy-3-(2-methylbutynyl-3-amino-2)-2-propanol . HCl (according to process [a]) (I, $R_1$ = 3-$CH_3$, $R_2$ and $R_3$ = H, $R_4$ and $R_5$ = $CH_3$)

8.2 Grams (0.05 mol) of 1-m-tolyloxy-2,3-epoxypropane were dissolved in 90 ml of ethanol, and after addition of 6.25 gm (0.075 mol) of 2-methyl-2-aminebutyne-3, the mixture was refluxed for two hours. After distilling off the solvent, the residue was recrystallized from ethyl acetate under addition of petroleum ether. The crystalline base was dissolved in acetonitrile; alchoholic HCl was added and crystallization was started under addition of ether. 6.5 Grams of colorless crystals were obtained, which are chromatographically pure. M.p. 139° to 141° C.

EXAMPLE 3

1-(2-Allylphenoxy)-3-(2-methylbutynyl-3-amino-2)-2-propanol,oxalate (according to process [a]) (I, $R_1$ = 2-allyl, $R_2$ and $R_3$ = H, $R_4$ and $R_5$ = $CH_3$)

9.5 Grams (0.05 mol) of 1-(2-allylphenoxy)-2,3-epoxypropane were dissolved in 60 ml of methanol. 8.3 gm (0.1 mol) of 2-methyl-2-amine-butyne-3 were added and the mixture was refluxed for three hours. After having distilled off the solvent, the basic residue was dissolved in acetone and a solution of 6 gm of oxalic acid was added. The precipitating crystalline oxalate was recrystallized from acetone once more. Yield: 4.7 gm, m.p. 144° to 146° C.

Analogous to the Examples 1 to 3, the following compounds of formula I are produced in line with process (a), e.g. by reacting the correspondingly substituted 1-phenoxy-2,3-epoxypropane according to formula II with the corresponding amine according to formula III in ethanol.

TABLE

| $R_1$ | $R_2$ | $R_3$ | $R_4$ | $R_5$ | M.P. of HCl-Salt in Case Nothing Else Indicated °C |
|---|---|---|---|---|---|
| 3-$CH_3$ | H | H | $C_2H_5$ | $C_2H_5$ | 143–145 |
| 2-O—$CH_2$—CH=$CH_2$ | H | H | $C_2H_5$ | $C_2H_5$ | 112–113 |
| 2-$CH_2$—CH=$CH_2$ | H | H | $C_2H_5$ | $C_2H_5$ | 128–129 |
| H | 2,3-CH=CH—CH=CH— | | $CH_3$ | $CH_3$ | 159–161 |
| 2-O—$CH_2$—CH=$CH_2$ | H | H | $CH_3$ | $CH_3$ | 100–103 |
| 3-$CH_3$ | H | H | —($CH_2$)$_5$— | | 159–160 |
| 2-$CH_2$—CH=$CH_2$ | H | H | —($CH_2$)$_5$— | | 120–122 |
| 2-Br | H | H | $CH_3$ | $CH_3$ | 138–139 |
| 4-$NO_2$ | H | H | $CH_3$ | $CH_3$ | 183–184 |
| 4-$CH_2$OH | H | H | $CH_3$ | $CH_3$ | 108–110 (Base) |
| 2-$OCH_3$ | H | H | $CH_3$ | $CH_3$ | 161–163 |
| 4-$COOCH_3$ | H | H | $CH_3$ | $CH_3$ | 127–129 |
| H | 3,4-($CH_2$)$_3$— | | $CH_3$ | $CH_3$ | 139–140 |
| 4-Tert. $C_4H_9$ | H | H | $CH_3$ | $CH_3$ | 146–147 |
| 2-iso $C_3H_7$ | H | H | $CH_3$ | $CH_3$ | 157–158 |
| 2-C≡CH | H | H | $CH_3$ | $CH_3$ | 165–167 |
| 4-NH—CO—$NHCH_3$ | H | H | $CH_3$ | $CH_3$ | 107–109 (Base) |
| 4-NH—CO—N($C_2H_5$)$_2$ | H | H | $CH_3$ | $CH_3$ | 125–127 |
| 4-$CH_2$—CO—$NH_2$ | H | H | $CH_3$ | $CH_3$ | 107–110 (Base) |
| 3-($C_2H_5$)$_2$N— | H | H | $CH_3$ | $CH_3$ | 134–137 (dihydrochloride) |
| 4-COOH | H | H | $CH_3$ | $CH_3$ | 159–162 |
| 4-NH—$COCH_3$ | H | H | $CH_3$ | $CH_3$ | 137–138 (Base) |
| 2-$CH_2$OH | H | H | $CH_3$ | $CH_3$ | 150–152 (Oxalate) |
| 2-$C_6H_{11}$ | H | H | $CH_3$ | $CH_3$ | 150–152 |
| 2-Cl | 4-Cl | H | $CH_3$ | $CH_3$ | 170–171 |
| 3-Cl | H | H | $CH_3$ | $CH_3$ | 142–144 |
| 2-$CONH_2$ | H | H | $CH_3$ | $CH_3$ | 230–233 |
| 3-Br | 4-$NH_2$ | 5-Br | $CH_3$ | $CH_3$ | 183–185 |

TABLE-continued

| $R_1$ | $R_2$ | $R_3$ | $R_4$ | $R_5$ | M.P. of HCl-Salt in Case Nothing Else Indicated °C |
|---|---|---|---|---|---|
| | | | | | (dihydrochloride) |
| 2-C≡C—CH$_3$ | H | H | CH$_3$ | CH$_3$ | 164–166 |
| H | 3,4-O—(CH$_2$)—O— | | CH$_3$ | CH$_3$ | 175–176 |
| 4-CO—C$_2$H$_5$ | H | H | CH$_3$ | CH$_3$ | 149–151 |
| 4-OH | H | H | CH$_3$ | CH$_3$ | 136–137.5 |
| | | | | | (Base) |
| 2-C$_6$H$_5$ | H | H | CH$_3$ | CH$_3$ | 157–158 |
| 2-Cl | H | H | CH$_3$ | CH$_3$ | 150–151 |

EXAMPLE 4

1-(2-Allyloxyphenoxy)-3-(2-methylbutynyl)-3-amino-2)-2-propanol . HCl (according to process [b]) (I, $R_1$ = 2—OCH$_2$CH=CH$_2$, $R_2$ and $R_3$ = H, $R_4$ and $R_5$ = CH$_3$)

2.4 Grams (0.025 mol) of tetrahydropyran were dropped slowly into 6.42 gm (0.025 mol) of 1-(2-allyloxyphenoxy)-3-bromo-2-propanol and a catalytical quantity of p-toluenesulfonic acid at 20° to 25° C. Then the mixture was heated for 30 minutes to 40° C, dissolved in 40 ml of benzene, and 5 gm (0.06 mol) of 2-methyl-2-amine-butyne-3 were added to it. The mixture was refluxed for two hours; then the solvent was distilled off and the residue was heated for 15 minutes with diluted hydrochloric acid to 80° C. After cooling off, it was extracted from ether and the aqueous phase was adjusted alkaline by NaOH. The precipitating basic portions were taken up in ether. The organic phase was dried with MgSO$_4$ and after filtering the ether was distilled off. The residue was dissolved in little ethanol. Etheric HCl was added and the crystalline hydrochloride recrystallized twice. M.p. 99° to 102° C.

EXAMPLE 5

1-(4-Nitrophenoxy)-3-(2-methylbutynyl-3-amino-2)-2-propanol .HCl (according to process [c]) (I, $R_1$ = 4-NO$_2$, $R_2$ and $R_3$ = H, $R_4$ and $R_5$ = CH$_3$)

2.7 Grams (approximately 0.008 mol) of 1-(4-nitrophenoxy)-3-(N-acetyl-2-methylbutynyl-3-amino-2)-2-propanol were refluxed in 25 ml of ethanol with 1 gm of KOH for two hours. After having distilled off the solvent, a viscous residue remained, which was treated with diluted HCl. After shaking out with chloroform, the aqueous phase was adjusted alkaline with NaOH and the precipitating amine was taken up in chloroform. After drying over NaSO$_4$, the solvent was distilled off and the residue was recrystallized from ethyl acetate under addition of petroleum ether. Yield: 1.5 gm, m.p. 125° to 127° C (base). Mixed melting point with substance obtained according to process (a): 126° to 127° C.

EXAMPLE 6

1-(4-Aminophenoxy)-3-(2-methylbutynyl-3-amino-2)-2-propanol . HCl (according to process [e]) (I, $R_1$ = 4-NH$_2$, $R_2$ and $R_3$ = H, $R_4$ and $R_5$ = CH$_3$)

A mixture of 8.1 gm of tin-II chloride in 20 ml of conc. HCl was heated to 60° C and 2.62 gm (0.01 mol) of 1-(4-nitrophenoxy)-3-(2-methylbutynyl-3-amino-2)-2-propanol were added in portions, so that the temperature did not exceed 65° C. After the addition had been finished, the mixture was stirred for 30 minutes and after cooling off it was adjusted alkaline with NaOH. The precipitating basic portions were shaken with chloroform. The chloroform solution was washed with water and dried over Na$_2$SO$_4$. After distilling off the CHCl$_3$, a solid residue remained, which was recrystallized from ethyl acetate under addition of petroleum ether.

Yield: 1.4 gm, m.p. 122° to 123° C (base).

According to process (e), the compound 1-(4-hydroxyphenoxy)-3-(2-methylbutynyl-3-amino-2)-2-propanol was made by heating the compound 1-(4-diethylaminocarbonyloxypheny)-3-(2-methylbutynyl-3-amino-2)-2-propanol (m.p. of hydrochloride: 126° C) in the presence of concentrated aqueous HCl. M.p. of the end product (base) is 136° to 137.5° C.

EXAMPLE 7

1-(4-Hydroxycarbonylphenoxy)-3-(2-methylbutynyl-3-amino-2)-2-propanol . HCl (according to process [e]) (I, $R_1$ = R-COOH, $R_2$ and $R_3$ = H, $R_4$ and $R_5$ = CH$_3$)

5 Grams of 1-(4-ethoxycarbonylphenoxy)-3-(2-methylbutynyl-3-amino-2)-2-propanol hydrochloride were refluxed in 30 ml of conc. HCl for two hours. After cooling, the crystalline mass that originated by hydrolysis was vacuum filtered and recrystallized twice from ethanol under addition of ether. Yield: 3.1 gm, m.p. 159° to 162° C.

EXAMPLE 8

1-(3,5-Dibromo-4-aminophenoxy)-3-(2-methylbutynyl-3-amino-2)-2-propanol . 2 HCl (according to process [f]) (I, $R_1$ = 4-NH$_2$, $R_2$ = 3-Br, $R_3$ = 5-Br, $R_4$ and $R_5$ = CH$_3$)

4.96 Grams (0.02 mol) of 1-(4-aminophenoxy)-3-(2-methylbutynyl-3-amino-2)-2-propanol were added into a mixture of 30 ml of HBr (65%) and 10 ml of water and heated to 45° C. While stirring and cooling, 4.54 gm (0.04 mol) of H$_2$O$_2$, 30%, were dropped into the mixture in such a way that the temperature did not rise over 65° C. After it had been kept at approximately 65° C for a further 30 minutes, the crystalline substance was vacuum filtered after cooling. It was then recrystallized from ethanol under addition of ether. Then the hydrochloride was dissolved in water. NaOH was added. The base was extracted with CHCl$_3$ and, after evaporation of the solvent, recrystallized from ethyl acetate under addition of petroleum ether. The chromatographically pure base was dissolved in ethanol; alcoholic HCl was added and the dihydrochloride was brought to crystallization under addition of ether.

Yield: 3.8 gm, m.p. 183° to 185° C.

EXAMPLES OF FORMULATIONS

| 1. Tablets | |
|---|---|
| 1-(4-aminophenoxy)-3-(2-methyl-butynyl-3-amino-2)-2-propanol . HCl | 40.0 parts |
| Corn starch | 164.0 parts |
| Sec. calcium phosphate | 240.0 parts |
| Magnesium stearate | 1.0 parts |
| | 445.0 parts |

Production:

The individual components were admixed well and the mixture was granulated in the usual way. The granulated in the usual way. The granulate was pressed into tablets of 445 mg by weight, of which each contains 40 mg of active ingredient.

| 2. Gelatin Capsules | |
|---|---|
| The content of the capsules was composed as follows: | |
| 1-(2-ethynylphenoxy)-3-(2-methyl-butynyl-3-amino-2)-2-propanol . HCl | 25.0 parts |
| Corn starch | 175.0 parts |
| | 200.0 parts |

Production:

The active ingredients of the content of capsule were mixed well and 200 mg portions of the mixture were filled into gelatin capsules of suitable size. Each capsule contains 25 mg of the active ingredient.

| 3. Injection Solution | |
|---|---|
| The solution was produced of the following ingredients: | |
| 1-(2-allylphenoxy)-3-(2-methylbutynyl-3-amino-2)-2-propanol . HCl | 2.5 parts |
| Sodium salt of EDTA (ethylene-diaminetetraacetic acid) | 0.2 parts |
| Distilled water ad | 100.0 parts |

Production:

The active ingredient and EDTA-salt were dissolved in sufficient water and filled with water to the desired volume. The solution was filtered free from suspended particles and filled into ampoules under aseptic conditions. Finally, the ampoules were sterilized and sealed. Each ampoule contains 25 mg of active ingredient.

Instead of the active ingredient mentioned in this example, 1-(2-hydroxymethylphenoxy)-3-(2-methylbutynyl-3-amino-2)-2-propanol. HCl in the same quantity may be used as well.

| 4. Coated Tablets with Sustained Release | |
|---|---|
| Core: | |
| (—)-1-(4-aminophenoxy)-3-(2-methylbutynyl-3-amino-2)-2-propanol . HCl | 25.0 parts |
| Carboxymethyl cellulose (CMC) | 295.0 parts |
| Stearic acid | 20.0 parts |
| Cellulose acetate/phthalate (CAP) | 40.0 parts |
| | 380.0 parts |

Production:

Active ingredient, CMC and stearic acid were mixed well and the mixture was granulated in the usual way, using a solution of the CAP in 200 ml of a mixture of ethanol/ethyl acetate. Then the granulate was pressed to 380 mg cores, coated in the conventional way with a sugary 5% solution of polyvinylpyrrolidone in water. Each coated tablet contains 25 mg of active ingredient.

| 5. Tablets | |
|---|---|
| 1-α-Naphthoxy-3-(3-ethylpentynyl-4-amino-3)-2-propanol . HCl | 35.0 gm |
| 2,6-bis-(diethanolamino)-4,8-di-piperidinopyrimido-[5,4-d]-pyrimidine | 75.0 gm |
| Lactose | 164.0 gm |
| Corn starch | 194.0 gm |
| Colloidal silicic acid | 14.0 gm |
| Polyvinylpyrrolidone | 6.0 gm |
| Magnesium stearate | 2.0 gm |
| Soluble starch | 10.0 gm |
| | 500.0 gm |

Instead of the β-adrenolytically active substances mentioned in this example, the substances 1-(2-allyloxyphenoxy)-3-(2-methylbutynyl-3-amino-2)-2-propanol. HCl and 1-(2-propargyloxyphenoxy)-3-(2-methylbutynyl-3-amino-2)-2-propanol. HCl may be used as well in the same quantity.

Production:

The active ingredient together with the lactose, corn starch, colloidal silicic acid and polyvinyl pyrrolidone was granulated after thorough mixing in the usual way, using an aqueous solution of the soluble starch. The granulate was admixed with the magnesium stearate and pressed into 1000 tablets each of 500 mg of weight, containing each 35 mg of the first and 75 mg of the second active ingredient.

The preceding specific embodiments are illustrative of the practice of the invention. It is to be understood, however, that other expedients known to those skilled in the art or disclosed herein may be employed without departing from the spirit of the invention and the scope of the appended claims.

We claim:

1. A 1-aryloxy-2-hydroxy-3-alkynylamino-propane selected from the group consisting of racemic or optically active compounds of the formula

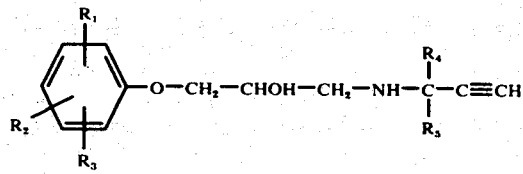

wherein $R_1$ is a member selected from the group consisting of hydrogen; halogen; nitro; alkyl having from 1 to 5 carbon atoms; alkoxy having from 1 to 4 carbon atoms; alkenyl having from 2 to 5 carbon atoms; alkynyl having from 2 to 5 carbon atoms; alkylamino having from 1 to 5 carbon atoms; dialkylamino having from 1 to 5 carbon atoms in each alkyl; alkoxyalkyl having from 2 to 6 carbon atoms; alkylaminoalkyl having from 2 to 6 carbon atoms; dialkylaminoalkyl having from 3 to 12 carbon atoms; —(CH$_2$)$_x$—NH$_2$ or —(CH$_2$)$_x$—OH, where $x$ is an integer from 0 to 3; alkynyloxy having from 3 to 6 carbon atoms; alkenyloxy having from 3 to 6 carbon atoms; —CO—R$_9$, where R$_9$ is a member selected from the group consisting of alkyl having 1 to 6 carbon atoms, phenylalkyl having 7 to 10 carbon atoms and phenyl; cycloalkyl having from 3 to 7 carbon atoms; phenyl; phenyl substituted with a substituent selected from the group consisting of halogen, lower alkyl, lower alkoxy and nitro; phenoxy; and phenoxy substituted with a substituent selected from the group consisting of halogen, lower alkyl, lower alkoxy and nitro;

$R_2$ is a member selected from the group consisting of hydrogen, halogen, alkyl having from 1 to 4 carbon atoms, alkoxy having from 1 to 4 carbon atoms, alkanoyl having from 2 to 4 carbon atoms, alkenyl having from 2 to 4 carbon atoms, amino and nitro;

$R_3$ is a member selected from the group consisting of hydrogen, halogen, alkyl having from 1 to 4 carbon atoms, alkoxy having from 1 to 4 carbon atoms and, together with $R_2$ in the ortho-position, —CH=CH—CH=CH— or —(CH$_2$)$_n$—, where $n$ is an integer from 3 to 5;

$R_4$ is a member selected from the group consisting of hydrogen and alkyl having from 1 to 3 carbon atoms; and $R_5$ is a member selected from the group consisting of alkyl having from 1 to 3 carbon atoms, and, together with $R_4$, —(CH$_2$)$_p$—, where p is an integer from 4 to 6; and physiologically compatible acid addition salts thereof.

2. The 1-aryloxy-2-hydroxy-3-alkynylamino-propanes of claim 1 wherein $R_4$ and $R_5$ are methyl and $R_1$, $R_2$ and $R_3$ have the values assigned in claim 1.

3. The 1-aryloxy-2-hydroxy-3-alkynylamino-propanes of claim 1 wherein $R_1$ is a member selected from the group consisting of alkenyl having from 2 to 5 carbon atoms, alkynyl having from 2 to 5 carbon atoms, alkenyloxy having from 3 to 6 carbon atoms and alkynyloxy having from 3 to 6 carbon atoms; $R_2$ and $R_3$ are members selected from the group consisting of hydrogen and alkyl having from 1 to 4 carbon atoms, and $R_4$ and $R_5$ have the values assigned in claim 1.

4. The 1-aryloxy-2-hydroxy-3-alkynylamino-propanes of claim 3 wherein $R_4$ and $R_5$ are methyl.

5. The 1-aryloxy-2-hydroxy-3-alkynylamino-propanes of claim 1 wherein $R_1$ is a member selected from the group consisting of allyl, ethynyl, propynyl, allyloxy and propargyloxy, $R_2$ and $R_3$ are hydrogen and $R_4$ and $R_5$ are methyl.

6. The 1-aryloxy-2-hydroxy-3-alkynylamino-propanes of claim 5 wherein $R_1$ is in the 2-position to the propanolamine side chain.

7. The 1-aryloxy-2-hydroxy-3-alkynylamino-propanes of claim 1 wherein $R_1$ is hydroxyalkyl having from 1 to 3 carbon atoms, $R_2$ and $R_3$ are hydrogen and $R_4$ and $R_5$ have the values assigned in claim 1.

8. The 1-aryloxy-2-hydroxy-3-alkynylamino-propanes of claim 7 wherein $R_1$ is hydroxymethyl.

9. The 1-aryloxy-2-hydroxy-3-alkynylamino-propanes of claim 7 wherein $R_4$ and $R_5$ are methyl.

10. The 1-aryloxy-2-hydroxy-3-alkynylamino-propanes of claim 1, wherein $R_1$ is amino, $R_2$ and $R_3$ are members selected from the group consisting of hydrogen, halogen and alkyl having from 1 to 4 carbon atoms, and $R_4$ and $R_5$ have the values assigned in claim 1.

11. The 1-aryloxy-2-hydroxy-3-alkynylamino-propanes of claim 1 wherein $R_1$ is 3-ethynyl, $R_2$ and $R_3$ are hydrogen and $R_4$ and $R_5$ are methyl.

12. The 1-aryloxy-2-hydroxy-3-alkynylamino-propanes of claim 1 wherein $R_1$ is 2-allyl, $R_2$ and $R_3$ are hydrogen and $R_4$ and $R_5$ are methyl.

13. The 1-aryloxy-2-hydroxy-3-alkynylamino-propanes of claim 1 wherein $R_1$ is 4-amino, $R_2$ is 3-bromo, $R_3$ is 5-bromo, $R_4$ and $R_5$ are methyl.

14. The 1-aryloxy-2-hydroxy-3-alkynylamino-propanes of claim 1 wherein $R_1$ is 2-hydroxymethyl, $R_2$ and $R_3$ are hydrogen and $R_4$ and $R_5$ are methyl.

15. The 1-aryloxy-2-hydroxy-3-alkynylamino-propanes of claim 1 wherein $R_1$ is 3-chloro, $R_2$ and $R_3$ are hydrogen and $R_4$ and $R_5$ are methyl.

* * * * *